(12) United States Patent
Michel

(10) Patent No.: US 7,366,574 B2
(45) Date of Patent: *Apr. 29, 2008

(54) DEVICE FOR THE TRANSVENOUS CARDIOVERSION OF ATRIAL FIBRILLATION OR ATRIAL FLUTTER

(75) Inventor: Ulrich Michel, Kaiserslautern (DE)

(73) Assignee: Cardiac Pacemakers, Inc., St. Paul, MN (US)

( * ) Notice: Subject to any disclaimer, the term of this patent is extended or adjusted under 35 U.S.C. 154(b) by 587 days.

This patent is subject to a terminal disclaimer.

(21) Appl. No.: 10/818,022

(22) Filed: Apr. 5, 2004

(65) Prior Publication Data

US 2004/0193240 A1    Sep. 30, 2004

Related U.S. Application Data

(60) Continuation of application No. 10/006,193, filed on Dec. 3, 2001, now Pat. No. 6,741,894, which is a continuation of application No. 09/528,680, filed on Mar. 20, 2000, now Pat. No. 6,438,416, which is a division of application No. 09/328,336, filed on Jun. 9, 1999, now Pat. No. 6,041,256, which is a continuation of application No. 08/807,519, filed on Feb. 27, 1997, now Pat. No. 5,913,887.

(30) Foreign Application Priority Data

Mar. 1, 1996 (DE) ............................ 296 03 805 U

(51) Int. Cl.
*A61N 1/00* (2006.01)

(52) U.S. Cl. ....................................... 607/123

(58) Field of Classification Search ........ 607/115–128, 607/4–8

See application file for complete search history.

(56) References Cited

U.S. PATENT DOCUMENTS

| 3,614,955 | A | 10/1971 | Mirowski | ............... 128/419 D |
| 3,804,098 | A | 4/1974 | Friedman | .................... 128/404 |

(Continued)

FOREIGN PATENT DOCUMENTS

DE   2827595   4/1979

(Continued)

OTHER PUBLICATIONS

Fain, et al., "A New Internal Defibrillation Lead System: Intrapericardial Placement Without Thoracotomy", *Circulation Supplement*, 76 (4), Abstracts from the 60th Scientific Sessions, Abstract No. 1839,(Oct. 1987), 1 p.

(Continued)

*Primary Examiner*—Scott M. Getzow
(74) *Attorney, Agent, or Firm*—Schwegman, Lundberg & Woessner, P.A.

(57) ABSTRACT

A transvenous catheter for the cardioversion of atrial fibrillation or atrial flutter and/or the stimulation of the heart's activity. The catheter has an electrically active section within a heart and an electrically passive section carrying electrical cables. At least two defibrillation electrodes are located in the electrically active section and coupled to the electrical cables of the catheter. Additionally, there are at least one sensing ring electrode positioned between the at least two defibrillation electrodes and coupled to the electrical cables.

9 Claims, 1 Drawing Sheet

U.S. PATENT DOCUMENTS

| | | | | |
|---|---|---|---|---|
| 3,942,536 A | 3/1976 | Mirowski et al. | ......... | 128/419 D |
| 4,030,508 A | 6/1977 | Thalen | ......... | 128/418 |
| 4,030,509 A | 6/1977 | Heilman et al. | ......... | 128/419 D |
| 4,106,512 A | 8/1978 | Bisping | ......... | 128/418 |
| 4,136,703 A | 1/1979 | Wittkampf | ......... | 128/419 P |
| 4,217,913 A | 8/1980 | Dutcher | ......... | 128/785 |
| 4,270,549 A | 6/1981 | Heilman | ......... | 128/784 |
| 4,291,707 A | 9/1981 | Heilman et al. | ......... | 128/784 |
| 4,311,153 A | 1/1982 | Smits | ......... | 128/785 |
| 4,463,765 A | 8/1984 | Gold | ......... | 128/785 |
| 4,548,203 A | 10/1985 | Tacker, Jr. et al. | ......... | 128/419 |
| 4,559,951 A | 12/1985 | Dahl et al. | ......... | 128/642 |
| 4,567,900 A | 2/1986 | Moore | ......... | 128/784 |
| 4,570,642 A | 2/1986 | Kane et al. | ......... | 128/785 |
| 4,603,705 A | 8/1986 | Speicher et al. | ......... | 128/786 |
| 4,624,265 A | 11/1986 | Grassi | ......... | 128/784 |
| 4,624,266 A | 11/1986 | Kane | ......... | 128/785 |
| 4,627,439 A | 12/1986 | Harris | ......... | 128/419 |
| 4,633,880 A | 1/1987 | Osypka et al. | ......... | 128/642 |
| 4,646,755 A | 3/1987 | Kane | ......... | 128/785 |
| 4,649,937 A | 3/1987 | DeHaan et al. | ......... | 128/784 |
| 4,649,938 A | 3/1987 | McArthur | ......... | 128/785 |
| 4,662,377 A | 5/1987 | Heilman et al. | ......... | 128/419 |
| 4,664,113 A | 5/1987 | Frisbie et al. | ......... | 128/344 |
| 4,727,877 A | 3/1988 | Kallok | ......... | 128/419 |
| 4,784,161 A | 11/1988 | Skalsky et al. | ......... | 128/785 |
| 4,799,486 A | 1/1989 | DuFault | ......... | 128/419 PG |
| 4,799,493 A | 1/1989 | DuFault | ......... | 128/705 |
| 4,817,608 A | 4/1989 | Shapland et al. | ......... | 128/419 |
| 4,817,634 A | 4/1989 | Holleman et al. | ......... | 128/784 |
| 4,819,661 A | 4/1989 | Heil, Jr. et al. | ......... | 128/786 |
| 4,819,662 A | 4/1989 | Heil, Jr. et al. | ......... | 128/786 |
| 4,827,932 A | 5/1989 | Ideker et al. | ......... | 128/419 D |
| 4,860,769 A | 8/1989 | Fogarty et al. | ......... | 128/784 |
| 4,865,037 A | 9/1989 | Chin et al. | ......... | 128/419 D |
| 4,886,074 A | 12/1989 | Bisping | ......... | 128/785 |
| 4,905,691 A | 3/1990 | Rydell | ......... | 606/47 |
| 4,924,881 A | 5/1990 | Brewer | ......... | 128/785 |
| 4,938,231 A | 7/1990 | Milijasevic et al. | ......... | 128/784 |
| 4,944,300 A | 7/1990 | Saksena | ......... | 128/419 D |
| 4,953,551 A | 9/1990 | Mehra et al. | ......... | 128/419 |
| 4,967,766 A | 11/1990 | Bradshaw | ......... | 128/785 |
| 4,971,070 A | 11/1990 | Holleman et al. | ......... | 128/784 |
| 4,998,975 A | 3/1991 | Cohen et al. | ......... | 128/419 D |
| 5,016,645 A | 5/1991 | Williams et al. | ......... | 128/784 |
| 5,016,646 A | 5/1991 | Gotthardt et al. | ......... | 128/784 |
| 5,016,808 A | 5/1991 | Heil, Jr. et al. | ......... | 228/176 |
| 5,020,544 A | 6/1991 | Dahl et al. | ......... | 128/784 |
| 5,044,375 A | 9/1991 | Bach, Jr. et al. | ......... | 128/786 |
| 5,050,601 A | 9/1991 | Kupersmith et al. | ......... | 128/419 D |
| 5,056,516 A | 10/1991 | Spehr | ......... | 128/419 |
| 5,063,932 A | 11/1991 | Dahl et al. | ......... | 128/639 |
| 5,076,285 A | 12/1991 | Hess et al. | ......... | 128/186 |
| 5,083,562 A | 1/1992 | de Coriolis et al. | ......... | 128/419 |
| 5,105,826 A | 4/1992 | Smits et al. | ......... | 128/784 |
| 5,107,834 A | 4/1992 | Ideker et al. | ......... | 128/419 |
| 5,111,811 A | 5/1992 | Smits | ......... | 128/419 D |
| 5,111,812 A | 5/1992 | Swanson et al. | ......... | 128/419 D |
| 5,129,404 A | 7/1992 | Spehr et al. | ......... | 128/785 |
| 5,133,353 A | 7/1992 | Hauser | ......... | 128/419 |
| 5,133,365 A | 7/1992 | Heil, Jr. et al. | ......... | 128/786 |
| 5,152,299 A | 10/1992 | Soukup | ......... | 128/785 |
| 5,165,403 A | 11/1992 | Mehra | ......... | 128/419 D |
| 5,174,303 A | 12/1992 | Schroeppel | ......... | 128/786 |
| 5,203,348 A | 4/1993 | Dahl et al. | ......... | 128/784 |
| 5,209,229 A | 5/1993 | Gilli | ......... | 128/419 D |
| 5,230,337 A | 7/1993 | Dahl et al. | ......... | 607/5 |
| 5,243,980 A | 9/1993 | Mehra | | |
| 5,259,394 A | 11/1993 | Bens | ......... | 607/127 |
| 5,259,395 A | 11/1993 | Li | ......... | 607/131 |
| 5,261,400 A | 11/1993 | Bardy | ......... | 607/5 |
| 5,269,319 A | 12/1993 | Schulte et al. | ......... | 128/786 |
| 5,271,417 A | 12/1993 | Swanson et al. | ......... | 607/122 |
| 5,282,845 A | 2/1994 | Bush et al. | ......... | 607/128 |
| 5,300,108 A | 4/1994 | Rebell et al. | ......... | 607/127 |
| 5,300,110 A | 4/1994 | Latterell et al. | ......... | 607/130 |
| 5,314,459 A | 5/1994 | Swanson et al. | ......... | 607/122 |
| 5,324,327 A | 6/1994 | Cohen | ......... | 607/122 |
| 5,342,414 A | 8/1994 | Mehra | ......... | 607/127 |
| 5,344,439 A | 9/1994 | Otten | ......... | 607/126 |
| 5,358,516 A | 10/1994 | Myers et al. | ......... | 607/116 |
| 5,366,496 A | 11/1994 | Dahl et al. | ......... | 607/132 |
| 5,374,286 A | 12/1994 | Morris | ......... | 607/119 |
| 5,383,908 A | 1/1995 | Sweeney et al. | ......... | 607/5 |
| 5,397,342 A | 3/1995 | Heil, Jr. et al. | ......... | 607/129 |
| 5,405,373 A | 4/1995 | Petersson et al. | ......... | 607/121 |
| 5,411,544 A | 5/1995 | Mar et al. | ......... | 607/122 |
| 5,425,755 A | 6/1995 | Doan | ......... | 607/119 |
| 5,425,756 A | 6/1995 | Heil, Jr. et al. | ......... | 607/128 |
| 5,447,533 A | 9/1995 | Vachon et al. | ......... | 607/120 |
| 5,447,534 A | 9/1995 | Jammet | ......... | 607/127 |
| 5,456,706 A | 10/1995 | Pless et al. | ......... | 607/122 |
| 5,456,708 A | 10/1995 | Doan et al. | ......... | 607/127 |
| 5,476,501 A | 12/1995 | Stewart et al. | ......... | 607/127 |
| 5,492,119 A | 2/1996 | Abrams | ......... | 128/642 |
| 5,500,008 A | 3/1996 | Fain | ......... | 607/5 |
| 5,522,874 A | 6/1996 | Gates | ......... | 607/127 |
| 5,531,780 A | 7/1996 | Vachon | ......... | 607/120 |
| 5,534,022 A | 7/1996 | Hoffmann et al. | ......... | 607/122 |
| 5,545,205 A | 8/1996 | Schulte et al. | ......... | 607/123 |
| 5,554,178 A | 9/1996 | Dahl et al. | ......... | 607/122 |
| 5,578,068 A | 11/1996 | Laske et al. | ......... | 607/126 |

FOREIGN PATENT DOCUMENTS

| | | | | |
|---|---|---|---|---|
| EP | 0057877 | 8/1982 | ......... | 607/121 |
| EP | 0211166 | 2/1987 | | |
| EP | 0452278 | 10/1991 | | |
| EP | 0460324 | 12/1991 | | |
| EP | 0573275 | 12/1993 | | |
| EP | 0612538 | 8/1994 | | |
| EP | 0620024 | 10/1994 | | |
| EP | 0672431 | 9/1995 | | |
| FR | 2588758 | 4/1987 | | |
| GB | 2032278 | 6/1980 | | |
| GB | 2240721 | 8/1991 | | |
| JP | 3-168161 | 7/1991 | | |
| JP | 4-40966 | 2/1992 | | |
| WO | WO-89/06148 | 7/1989 | | |
| WO | WO-92/07616 | 5/1992 | | |

OTHER PUBLICATIONS

Jones, D. L., et al., "Internal Cardiac Defibrillation in Man: Pronounced Improvement with Sequential Pulse Delivery to Two Different Lead Orientations", *Circulation*, 73 (3), (Mar. 1986),pp. 484-491.

Alt, Eckhard, et al., "Initial Experience with Intracardiac Atrial Defibrillation in Patients with Chronic Atrial Fibrillation", *PACE, vol. 17, Part II*, (May 1994,), 1067-1078.

Desilva, R. A., et al., "Cardioversion and defibrillation.", *Am Heart J.*, 100(6 Pt 1), (Dec. 1980),881-95.

Ewy, Gordon A., "Optimal Technique for Electrical Cardioversion of Atrial Fibrillation", *Circulation, vol. 86, No. 5*, (Nov. 1992),1645-1647.

Levy, S., "A randomized comparison of external and internal cardioversion of chronic atrial fibrillation", *Circulation*, 86(5), (Nov. 1992),1415-20.

Lown, B., "Electrical reversion of cardiac arrhythmias", *Br Heart J.*, 29(4), (Jul. 1967),469-89.

Lown, B., et al., "New method for terminating cardiac arrhythmias. Use of synchronized capacitor discharge", *JAMA*, 182, (Nov. 3, 1962),548-55.

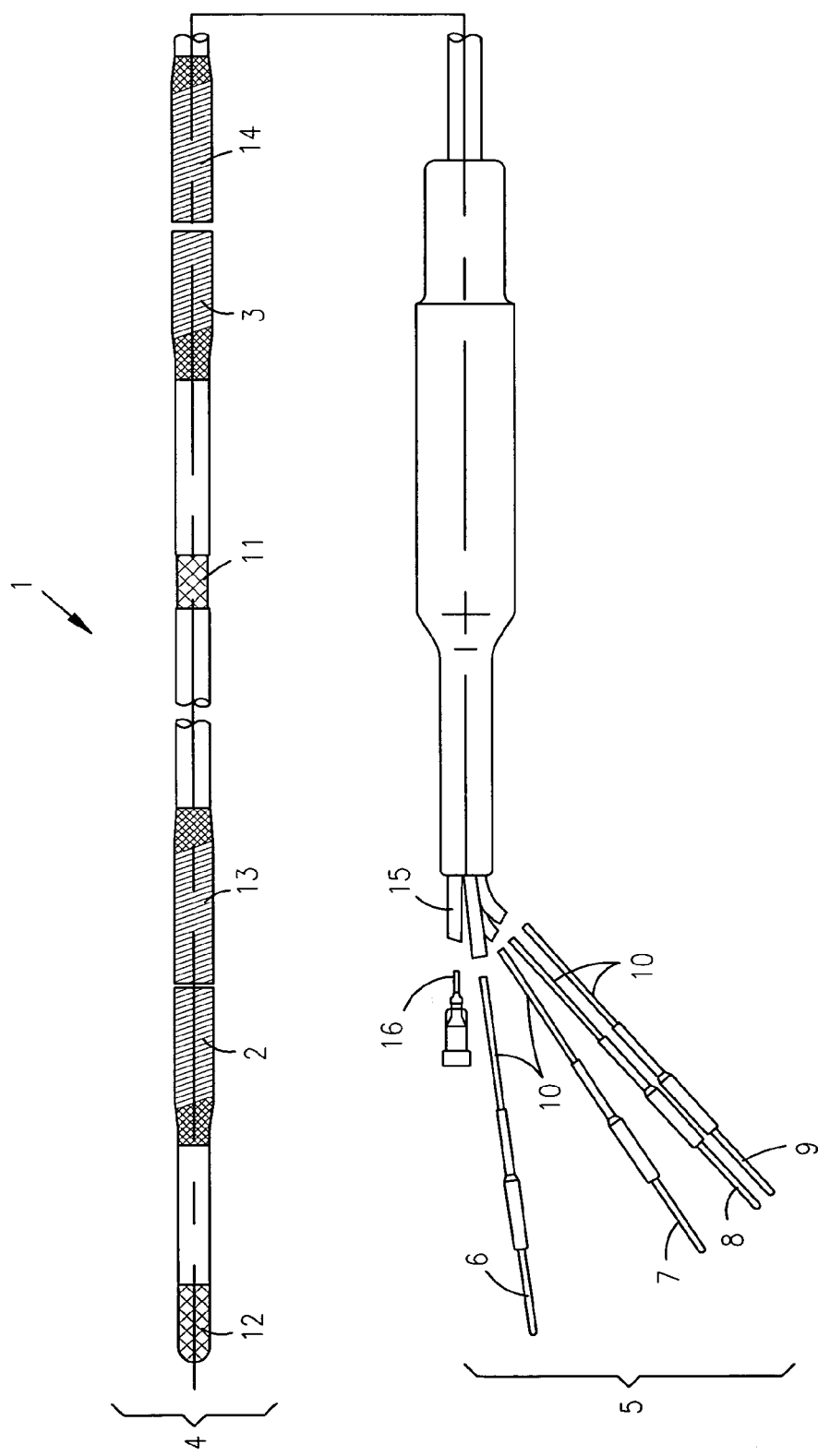

DEVICE FOR THE TRANSVENOUS CARDIOVERSION OF ATRIAL FIBRILLATION OR ATRIAL FLUTTER

CROSS-REFERENCE TO RELATED APPLICATION(S)

This application is a continuation of U.S. patent application Ser. No. 10/006,193, filed on Dec. 3, 2001, now issued as U.S. Pat. No. 6,741,894, which is a continuation of U.S. patent application Ser. No. 09/528,680, filed on Mar. 20, 2000, now issued as U.S. Pat. No. 6,438,416, which is a division of U.S. patent application Ser. No. 09/328,336, filed on Jun. 9, 1999, now issued as U.S. Pat. No. 6,041,256, which is a continuation of U.S. patent application Ser. No. 08/807,519, filed on Feb. 27, 1997, now issued as U.S. Pat. No. 5,913,887, the specifications of which are incorporated herein by reference.

TECHNICAL FIELD

The present invention relates generally to implantable medical devices and in particular to an implantable transvenous catheter as well as an analysis, pacemaker and/or defibrillation unit.

BACKGROUND OF INVENTION

A disorder having a rapid, irregular sequence of heart beats resulting from a disordered electrical excitation of the atria, is known as atrial fibrillation or atrial flutter. A distinction is made between paroxysmal (sudden) and persistent (chronic) arrhythmia. Some of these arrhythmia types may be treated by medications while others must be treated by external cardioversion. For this latter treatment, a high quantity of energy is output through the external area of the body, conventionally under anesthetic to restore the normal cardiac rhythm (sinus rhythm). Several studies have managed to show that the transvenous cardioversion of atrial fibrillation and/or atrial flutter can be performed with a considerably lower energy level than if the energy is applied to the external area of the body.

The use of an energy quantity of 200 J in an initial phase of treatment for external cardioversion and, in the event of its failure, two further pulses of 360 J, is proposed by Gordon A. Ewy as the optimal form of therapy in his article entitled "Optimal Technique for Electrical Cardioversion of Atrial Fibrillation", Circulation, pp. 1645 ff, Volume 86, No. 5, November 1992. Despite these high levels of energy output, Ewy emphasizes that great care must be given to ensuring the correct positioning and low transfer resistance of the external defibrillation electrodes, to achieve the best results.

As part of a comparative study, Levy et al. report in their publication entitled "A Randomized Comparison of External and Internal Cardioversion of Chronic Atrial Fibrillation", Circulation, pp. 1415-20, Volume 86, No. 5, November 1992, on the results of external and internal cardioversion and come to the conclusion that internal cardioversion is more effective for the restoration of the sinus rhythm without involving any increased risks. Internal cardioversion was completed for this study using a catheter fitted with an electrode together with an external thorax electrode.

E. Alt, C. Schmitt, R. Ammer, M. Coenen, P. Fotuhi, M. Karch and R. Blasini present a method of therapy for treating arrhythmia in their article entitled "Initial Experience with Intracardiac Atrial Defibrillation in Patients with Chronic Atrial Fibrillation", PACE, Volume 17, May 1994, Part II, in which an initial catheter fitted with a distal electrode is inserted in the Coronary Sinus in a catheter laboratory with X-ray monitoring, and a second catheter, also fitted with a distal electrode, is positioned in the right atrium. With this form of therapy, too, low levels of energy were used to remedy both spontaneous as well as induced atrial fibrillation, essentially with no negative effects.

Although the transvenous forms of therapy are not only far superior in terms of the levels of output energy compared to methods which use externally applied electrodes, there have been major effects to achieve further improvements in the therapy and in the equipment used for it.

A process of this nature in clinical emergency should provide extremely short preparation times and place as little stress as possible on the patient. Furthermore, the safety involved with this type of therapy should be increased. Although costs are of lesser importance in this particular area, they are becoming increasingly significant recently as a result of the wide range of efforts to make savings.

SUMMARY OF THE INVENTION

Using the transvenous catheter proposed by the invention, it is now possible to perform both defibrillation and the detection and stimulation to correct abnormal cardiac functioning, such as arrhythmias, essentially using a single catheter. The catheter, also known in clinical practice as a "single electrode," can be inserted into the heart quickly and safely, for example by means of puncturing a vein. In initial applications, the catheter proposed by the invention was positioned correctly with an X-ray exposure time of, on average, 4.8 to 5.5 minutes and then started. By further practice and with additional experience, it is assumed that these times can be reduced to a range from one to three minutes, so that both for intensive medical, operative and post-operative emergency situations, rapid initial care can be ensured.

It should also be emphasized that the invention proposes that the catheter can be inserted and correctly positioned by a single operator so that the interaction of several operators for the coordinated positioning of several electrodes is not necessary.

Another particular advantage of the catheter proposed by the invention is that adequate spacing between the electrodes is also ensured as a result of the axial spacing of a proximal electrode from a distal electrode to ensure that the interaction length does not fall below the minimum for the treatment. The axial spacing can be adjusted by means of producing a defibrillation axis which is ideal for the atrium, namely between the right-hand atrium and the coronary sinus. The catheter proposed by the invention stabilizes this position by means of its longitudinal structure which means that essentially no further means of fastening are required to hook the electrodes into the tissue, but such means may be used if desired.

Even in a floating mode, without direct tissue contact, it may always be assumed that the catheter proposed by the invention will not suffer a short circuit as a result of the axial spacing of the electrodes and that detection, stimulation and cardioversion or defibrillation can always be performed safely.

Both psychologically and physically the catheter proposed by the invention presents considerably less stress for the patient. Only a single incision is required and the temporal and medication stress is also less.

One embodiment of the present invention is a disposable catheter to reduce cost.

In one embodiment, the distal electrode and proximal electrode positioned in the electrically active section of the catheter has a spacing of between 10 and 100 mm between each other. This means that consideration may be given on the one hand to the size of the heart and on the other to the symptoms of the individual case. In this embodiment, the axial spacing is around 85 mm.

Spiral electrodes have proved to be particularly beneficial for use as the proximal and distal electrodes. This electrode design offers a high level of flexibility, good position-retaining characteristics and a large electrical interaction area. This means that it was possible with a proximal electrode just 55 mm in length and a distal electrode just 45 mm in length to create an electrically active overall area of 1040 mm². Compared to the levels of energy used with conventional treatments of 200 to 300 Joules per defibrillation process, it was possible to achieve reliable defibrillation using the device proposed by the invention with an energy level of just 1 to 8 Joules. Even when used on patients who are resistant to external cardioversion, it was possible to remedy atrial flutter with an output energy level of 2 to 20 Joules.

With a ring electrode positioned between the proximal and distal electrodes, it is also possible to monitor and analyze and stimulate the heart activity at the same time as and/or at a different time to the electrically active conditions.

The electrically passive section of the catheter, in one embodiment, consists of external electrical connections at the end away from the heart which can be used to connect an external heart pacemaker, an analysis and/or defibrillation unit. This means that the equipment which already exists in a hospital can continue to be used.

In particular, fluid-sealed electrical connections can be used with implantable units in the manner proposed by the invention.

In another embodiment, on the proximal end of the electrically active section of the catheter, there is a cap at a spacing from the distal electrode. This provides the correct axial spacing of the distal electrode, in particular, from the base of the right-hand atrium, and also allows the electrodes to be secured in position. In one embodiment, the cap is a blind cap.

If the cap is designed in the form of a further electrode, the monitoring and analysis functions as well as the stimulation of the heart can be performed from a remote point. The electrical activity may be recorded and evaluated at least in two sections. Furthermore, the proximal and/or the distal electrode may be split into separate areas and alternatively or additionally fitted with electrical cables and connectors to allow even better monitoring and analysis as well as extended forms of therapy.

The catheter proposed by the invention may be inserted in a particularly simple manner if a stylet duct extends over the length of the catheter and is fitted with a malleable stylet wire. The stylet wire can be moved axially within the stylet duct and is a flexible metallic rod or wire which can retain a desired imparted shape and is inserted in the stylet duct of the catheter to stiffen it and give it form during its passage through the vasculature.

It should be pointed out that in the sense proposed by the invention, the term "catheter" refers not only to a probe which is inserted for a limited period which is fitted with electrical connectors and contacts, but also any form of chronic or permanently implanted probe of that nature with electrically controllable electrodes and the relevant connectors. Furthermore, the term "analysis" in conjunction with the invention is intended to comprise the functions of monitoring, recording, storing, evaluation and/or transferring data to additional function modules from implanted or external units.

BRIEF DESCRIPTION OF THE DRAWINGS

FIG. 1 is a view of the catheter proposed by the invention together with its main components.

DETAILED DESCRIPTION

The invention is described in the following on the basis of one embodiment of the invention shown in FIG. 1. The transvenous catheter which is denoted in full with 1, comprises a distal electrode 2 and a proximal electrode 3 which are positioned in the electrically active section 4 of the catheter 1 shown in the top section of the drawing in FIG. 1. The electrically passive section 5 of the catheter 1 shown in the bottom section of FIG. 1 comprises electrical connections 6, 7, 8, and 9, which are connected by their respective cables 10 to the modules in the electrically active section 4. The connections 6, 7, 8, and 9 can be connected in the conventional manner to an external analysis, pacemaker and/or defibrillation unit.

Alternatively, an implantable analysis, pacemaker and/or defibrillation unit may be connected to the electrically passive section 5 in a fluid-sealed manner.

The electrically active section 4 is essentially the section of the catheter 1 whose modules, when operational, are positioned in or near the heart receiving the treatment. The electrically passive section 5 of the catheter is the other section of the catheter 1 which, however, does not generate any electrophysiological interaction with the tissue receiving the treatment.

The electrophysiological effect which is predominantly generated by electrodes 2 and 3, which take the form of spiral electrodes, may be monitored by a ring electrode 11 positioned between these electrodes 2 and 3. Both electrode 2 and electrode 3 may be used as the reference potential for the voltage which is measured on the electrode 11. Furthermore, it is within the scope of the invention that electrical signals are output from the electrodes 2, 3 and 11 and from an electrode 12 which takes the form of a cap, to obtain information about the heart's activity.

However, a suitable method is to measure the potential between the ring electrode 11 and the proximal electrode 3. Furthermore, it is within the scope of the invention, to refine the measurement data, to split one or both electrodes 2, 3 into further electrode areas 13, 14 which are equipped with separate cables and connectors.

Essentially, parallel to the electrical cables 10 there is a stylet duct 15 in which a malleable wire 16 can be inserted in such a way that it may be moved longitudinally along the duct. Using the malleable wire 16, when inserting the catheter 1, it is possible to overcome any obstacles or geometries in the body more easily and quickly using the defined shape imparted in the wire 16. After the correct placement of the catheter 1, either the stylet duct 15 or an additional duct which is not shown in the drawing but which has a mechanical feed to the cap, on which in this case an outfeed aperture may be located, can be used to administer local doses of medications which assist with the treatment.

Without restricting the general nature of the invention, the following are the sizes of the catheter proposed by the invention. The axial extension of the cap 12 may be 4 mm and its distance from the distal electrode may be around 10 mm. A length of the distal spiral electrode of 45 mm and of the proximal electrode of 55 mm will provide an electrically active area of around 1040 mm$^2$ whereby the spacing between the distal (2) and the proximal (3) electrodes is 85 mm. In particular, this last spacing distance may vary depending on the size of the heart being treated. It is within the scope of the invention to provide the treating doctor with a set of catheters tailored to the various sizes of hearts. The ring electrode 11 which extends in the axial direction over a length of around 3 mm is 12 mm away from the proximal electrode and 70 mm from the distal electrode 2. All these distances refer not to the respective center but to the nearest edge of the module concerned.

A catheter with the above dimensions could be used successfully for defibrillation at energy levels of 1 to 8 Joules, or for patients who are resistant to external cardioversion, with levels of 8 to 20 Joules.

It is also within the scope of the invention to make the catheter 1 together with an external or implantable analysis, pacemaker and/or defibrillation unit.

In addition to the rapid intensive medical initial care, the forms of therapy include treatment in a cardiological catheter laboratory and the post-operative monitoring and treatment of patients who have undergone open heart surgery or heart transplants. Particularly in this last case, arrhythmia occurs frequently, sometimes with a life-threatening character. Patients fresh from the operating theater who in the past have normally had to be defibrillated externally with unhealed wounds, can now be treated with uninterrupted monitoring using minimal levels of energy. Furthermore, the catheter proposed by the invention allows the uninterrupted recording of the post-operative clinical picture.

As a result of the intensive monitoring facilities and the immediate reaction to correct rhythmic stimulation, cardioversion or defibrillation, it is expected that medications can be administered with considerably lower dosages. Particularly in view of the stresses suffered during the post-operative phase, it is also expected that stabilization and the restoration of the patients will also take place more quickly.

In addition to the positioning of the catheter 1 in the main vein for the return of the blood, the Coronary Sinus and the right-hand atrium, it is possible to defibrillate the ventricles of the heart (proximal electrode within the right-hand atrium and the distal electrode within the right ventricle) by connecting it to a ventricular cardioverter/defibrillator. This means that it is possible using the four electrodes (12 and 2, 13 as well as 11 and 3, 14) to record the electrical signals from the atria and the ventricles synchronously. Using the catheter proposed by the invention, therefore, it is possible to pace in the ventricle, sense in the ventricle and have an inhibited pacing response to the sensing (VVI). It is also possible to pace in both the ventricle and the atrium, sense in the ventricle and have an inhibited pacing response to the sensing (DVI). Also, it is possible to have pacing in the ventricle, a dual chamber detection with either an inhibited or a triggered pacing response to the sensing (VDD) is possible. At the same time, biatrial stimulation (right and left atrium) can be performed. Other configurations of pacing, sensing and pacing response to sensing are known in the art.

Another area of application is therapy for paroxysmal and chronic arrhythmia which offers the benefits of a permanent implant described above without a lengthy stay in a hospital.

The counterpart German Patent Application Ser. No. 296 03 805.9, filed Mar. 1, 1996, by Ulrich Michel, is hereby incorporated by reference in its entirety.

In this detailed description references were made to the accompanying drawing which forms a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. This detailed description is, therefore, not to be taken in a limiting sense, and the scope of the present invention is defined by the appended claims and equivalents thereof.

What is claimed is:

1. A method comprising:
   implanting a catheter within a right atrium and a coronary sinus, wherein the catheter includes a first electrode and a second electrode, and the first electrode is axially spaced from the second electrode where the first electrode is positioned within a right atrium when the second electrode is positioned within a coronary sinus and substantially adjacent to a left atrium;
   monitoring a first cardiac potential at the right atrium; and
   monitoring a second cardiac potential at the left atrium.

2. The method of claim 1 wherein monitoring the first cardiac potential at the right atrium includes measuring the potential between a sensing ring and the first electrode, wherein the sensing ring is positioned between the first electrode and the second electrode.

3. The method of claim 1, wherein monitoring the second cardiac potential at the left atrium includes measuring the potential between a sensing ring and the second electrode, wherein the sensing ring is positioned between the first electrode and the second electrode.

4. The method of claim 1, further comprising monitoring a third cardiac potential across the right atrium and the left atrium.

5. The method of claim 1, wherein monitoring the third cardiac potential across the right atrium and the left atrium includes measuring the potential between a cap electrode and the first electrode, wherein the cap electrode is positioned at the distal end of the catheter.

6. The method of claim 1, further comprising analyzing one of the first cardiac potential or the second cardiac potential for the occurrence of an atrial arrhythmia.

7. The method of claim 1, further comprising analyzing the first cardiac potential and the second cardiac potential for the occurrence of an atrial arrhythmia.

8. The method of claim 1, further comprising delivering atrial defibrillation energy with one of the first electrode or the second electrode.

9. The method of claim 1, further comprising delivering atrial defibrillation energy with the first electrode and the second electrode.

* * * * *